US011413306B2

(12) United States Patent
Dessen et al.

(10) Patent No.: US 11,413,306 B2
(45) Date of Patent: Aug. 16, 2022

(54) ALGINATE OLIGOMERS FOR THE TREATMENT OR PREVENTION OF MICROBIAL OVERGROWTH IN THE INTESTINAL TRACT

(71) Applicant: AlgiPharma AS, Sandvika (NO)

(72) Inventors: Arne Dessen, Røyken (NO); Philip Rye, Eiksmarka (NO)

(73) Assignee: ALGIPHARMA AS, Sandvika (NO)

( * ) Notice: Subject to any disclaimer, the term of this patent is extended or adjusted under 35 U.S.C. 154(b) by 0 days.

(21) Appl. No.: 15/766,272

(22) PCT Filed: Oct. 6, 2016

(86) PCT No.: PCT/EP2016/073931
§ 371 (c)(1),
(2) Date: Apr. 5, 2018

(87) PCT Pub. No.: WO2017/060388
PCT Pub. Date: Apr. 13, 2017

(65) Prior Publication Data
US 2019/0117683 A1 Apr. 25, 2019

(30) Foreign Application Priority Data
Oct. 6, 2015 (GB) ..................................... 1517639

(51) Int. Cl.
| | |
|---|---|
| *A61K 31/734* | (2006.01) |
| *A61P 31/10* | (2006.01) |
| *A61K 9/00* | (2006.01) |
| *A61K 45/06* | (2006.01) |
| *A61K 31/165* | (2006.01) |
| *A61K 31/404* | (2006.01) |
| *A61K 31/415* | (2006.01) |
| *A61K 31/4375* | (2006.01) |
| *A61K 31/47* | (2006.01) |
| *A61K 31/7036* | (2006.01) |
| *A61K 31/4178* | (2006.01) |
| *A61K 31/365* | (2006.01) |
| *A61K 31/4245* | (2006.01) |
| *A61K 31/352* | (2006.01) |
| *A61K 31/192* | (2006.01) |
| *A61K 36/03* | (2006.01) |
| *A61K 31/522* | (2006.01) |
| *A61K 31/4422* | (2006.01) |
| *A61P 31/04* | (2006.01) |

(52) U.S. Cl.
CPC .......... *A61K 31/734* (2013.01); *A61K 9/0029* (2013.01); *A61K 9/0053* (2013.01); *A61K 9/0073* (2013.01); *A61K 31/165* (2013.01); *A61K 31/192* (2013.01); *A61K 31/352* (2013.01); *A61K 31/365* (2013.01); *A61K 31/404* (2013.01); *A61K 31/415* (2013.01); *A61K 31/4178* (2013.01); *A61K 31/4245* (2013.01); *A61K 31/4375* (2013.01); *A61K 31/4422* (2013.01); *A61K 31/47* (2013.01); *A61K 31/522* (2013.01); *A61K 31/7036* (2013.01); *A61K 36/03* (2013.01); *A61K 45/06* (2013.01); *A61P 31/04* (2018.01); *A61P 31/10* (2018.01)

(58) Field of Classification Search
CPC .................................................... A61K 31/734
See application file for complete search history.

(56) References Cited

U.S. PATENT DOCUMENTS

| | | | |
|---|---|---|---|
| 5,169,840 A | 12/1992 | Otterlei et al. | |
| 6,121,441 A | 9/2000 | Simensen et al. | |
| 2009/0010914 A1* | 1/2009 | Taylor | A61K 9/007 |
| | | | 424/94.61 |

FOREIGN PATENT DOCUMENTS

| | | |
|---|---|---|
| CN | 1562071 A | 1/2005 |
| WO | WO 89/08448 A1 | 9/1989 |
| WO | WO 91/11205 A1 | 8/1991 |
| WO | WO 94/09124 A1 | 4/1994 |
| WO | WO 03/045402 A1 | 6/2003 |
| WO | WO 2004/011628 A1 | 2/2004 |
| WO | WO 2005/023176 A2 | 3/2005 |
| WO | WO 2006/002421 A2 | 1/2006 |
| WO | WO 2007/039754 A1 | 4/2007 |
| WO | WO 2007/039760 A2 | 4/2007 |

(Continued)

OTHER PUBLICATIONS

Fridge, J. et al., Journal of Pediatric Gastroenterology and Nutrition, "Risk Factors for Small Bowel Bacteria Overgrowth in Cystic Fibrosis", 2007, vol. 44, pp. 212-218 (Year: 2007).*
Nordgard, C. et al., Biomacromolecules, "Alterations in Mucus Barrier Function and Matrix Structure Induced by Guluronate Oligomers", 2014, vol. 15, pp. 2294-2300 (Year: 2014).*
De Lisle, R. C. et al., Am. J. Physiol. Gastrointest. Liver Physiol., "Effects of laxative and N-acetylcysteine on mucus accumulation, bacterial load, transit, and inflammation in the cystic fibrosis mouse small intestine", 2007, vol. 293, pp. G577-G584 (Year: 2007).*

(Continued)

*Primary Examiner* — Bahar Craigo
(74) *Attorney, Agent, or Firm* — Knobbe, Martens, Olson & Bear, LLP (57) ABSTRACT

The invention provides a method for the treatment or prevention of microbial overgrowth in at least part of the intestinal tract of a subject, said method comprising administering an effective amount of an alginate oligomer to a subject in need thereof. Also provided is an alginate oligomer for use in the treatment or prevention of microbial overgrowth in at least part of the intestinal tract of a subject and a product containing an alginate oligomer and further pharmaceutical for the treatment of intestinal microbial overgrowth and/or a CFTR modulator as a combined preparation for separate, simultaneous or sequential use in the treatment or prevention of microbial overgrowth in at least part of the intestinal tract of a subject.

12 Claims, 3 Drawing Sheets

(56) References Cited

FOREIGN PATENT DOCUMENTS

| WO | WO 2007/056341 A1 | 5/2007 |
|---|---|---|
| WO | WO 2007/134279 A2 | 11/2007 |
| WO | WO 2008/125828 A2 | 10/2008 |
| WO | WO 2009/038683 A2 | 3/2009 |
| WO | WO 2009/064959 A1 | 5/2009 |
| WO | WO 2009/068841 A2 | 6/2009 |
| WO | WO 2009/073757 A1 | 6/2009 |
| WO | WO 2009/076141 A2 | 6/2009 |
| WO | WO 2009/076142 A2 | 6/2009 |
| WO | WO 2010/019239 A2 | 2/2010 |
| WO | WO 2010/037066 A2 | 4/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/138484 A2 | 12/2010 |
| WO | WO 2010/139957 A1 | 12/2010 |
| WO | WO 2010/139959 A2 | 12/2010 |
| WO | WO 2011/019413 A1 | 2/2011 |
| WO | WO 2011/050325 A1 | 4/2011 |
| WO | WO 2011/072241 A1 | 6/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2011/133953 A1 | 10/2011 |
| WO | WO 2011/133956 A1 | 10/2011 |
| WO | WO 2011/146901 A1 | 11/2011 |
| WO | WO 2015/128495 A1 | 9/2015 |
| WO | WO 2016/151051 A1 | 9/2016 |

OTHER PUBLICATIONS

Vitko, M. et al., Journal of Cystic Fibrosis, "A novel guluronate oligomer improves intestinal transit and survival in cystic fibrosis mice", 2016, vol. 15, pp. 745-754 (Year: 2016).*
Database WPI 2005, Application No. 2005-306977 (XP-002765058).
Nordgard et al. 2011 "Oligosaccharides as modulators of rheology in complex mucous systems" *Biomacromolecules* 12: 3084-3090.
Pritchard et al. 2016 "A new class of safe oligosaccharide polymer therapy to modify the mucus barrier of chronic respiratory disease" *Molecular Pharmaceutics* 13: 863-872.
Vitko et al. 2016 "A novel guluronate oligomer improves intestinal transit and survival in cystic fibrosis mice" *J Cystic Fibrosis* 15: 745-751.
Wang et al. 2006 "In vivo prebiotic properties of alginate oligosaccharides prepared through enzymatic hydrolysis of alginate" *Nutrition Research* 26: 597-603.
Wang et al. 2015 "Inhibition of adhesion of intestinal pathogens (*Escherichia coli, Vibrio cholera, Campylobacter jejuni, and Salmonela typhimurium*) by common oligosaccharides" *Foodborne Pathogens and Disease* 12: 360-365.

Yan et al. 2011 "Sodium alginate oligosaccharides from brown algae inhibit *Salmonella enteritidis* colonization in broiler chickens" *Poultry Science* 90: 1441-1448.
Al-Khedairy, E.B.H, 2006, "In Vitro Release Study on Capsules and Tablets Containing Enteric-Coated Granules Prepared by Wet Granulation" Iraqi J.Pharm.Sci., vol. 15(1): 49 (in 4 pages).
De Lisle, 2007 "Altered transit and bacterial overgrowth in the cystic fibrosis mouse small intestine" Am J Physio Gastrointest Liver Physiol 293: G104-G111.
Derichs, N., 2013 "Targeting a genetic defect: cystic fibrosis transmembrane conductance regulator modulators in cystic fibrosis" Eur. Respir. Rev. 22(127): 58-65.
Ertesvåg, H., et al., 1999 "Mannuronan C-5-Epimerases and their application for in vitro and in vivo design of new alginates useful in biotechnology" Metabolic Engineering vol. 1, 262-269.
Gimmestad, M. et al., 2003 "The Pseudomonas fluorescens AlgG Protein, but Not Its Mannuronan C-5-Epimerase Activity, Is Needed for Alginate Polymer Formation" Journal of Bacteriology vol. 185(12) 3515-3523.
Gimmestad, M. et al., 2006 Identification and Characterization of an *Azotobacter vinelandii* Type I Secretion System Responsible for Export of the AlgE-Type Mannuronan C-5-Epimerases Journal of Bacteriology vol. 188(15): 5551-5560.
Nadkarni et al., 2002 "Determination of bacterial load by real-time PCR using a broad-range (universal) probe and primers set" Microbiology 148:257-266.
Norkina et al., 2004 "Bacterial overgrowth in the cystic fibrosis transmembrane conductance regulator null mouse small intestine" Infection and Immunity, vol. 72(10): 6040-6049.
Pedemonte, N., et al., 2005 "Small-molecule correctors of defective ΔF508-CFTR cellular processing identified by high-throughput screening" J Clin Invest. 2005;115(9):2564-2571.
Pedemonte, N., et al., 2005 "Phenylglycine and Sulfonamide Correctors of Defective ΔF508 and G551D Cystic Fibrosis Transmembrane Conductance Regulator Chloride-Channel Gating" Molecular Pharmacology, 2005 vol. 67 No. 5 1797-1807.
Petit, R.S. and Fellner, C., 2014 "CFTR Modulators for the Treatment of Cystic Fibrosis" Pharmacy and Therapeutics 39(7): 500-511.
Remminghorst and Rehm, 2006 "Bacterial alginates: from biosynthesis to applications" Biotechnology Letters vol. 28, 1701-1712.
Strugala et al., 2004 "Bioactive properties of epimerized alginates" Gums and Stabilisers for the Food Industry 12, The Royal Society of Chemistry, 84-94.
Van Goor, F. et al., 2006 "Rescue of ΔF508-CFTR trafficking and gating in human cystic fibrosis airway primary cultures by small molecules" Am J Physiol Lung Cell Mol Physiol 290: L1117-L1130.
Zhang, et al., 2004 "Preparation and structure elucidation of alginate oligosaccharides degraded by alginate lyase from *Vibro* sp. 510", Carbohydrate Research 339 (2004) 1475-1481.

* cited by examiner

ALGINATE OLIGOMERS FOR THE TREATMENT OR PREVENTION OF MICROBIAL OVERGROWTH IN THE INTESTINAL TRACT

FIELD OF THE INVENTION

The present invention relates to the treatment or prevention of microbial overgrowth in the intestinal tract, particularly the small intestine, using alginate oligomers. More specifically, the present invention relates to the treatment or prevention of small intestinal microbial overgrowth, or even more specifically, small intestinal bacterial overgrowth (SIBO) (also referred to as blind loop syndrome (BLS) and bacterial overgrowth syndrome (BOS)) using alginate oligomers. The invention is based on the finding that alginate oligomers, in particular if administered orally, may act to decrease intestinal tract transit time, including in subjects with intestinal motility disorders, especially subjects with reduced intestinal motility (i.e. where intestinal tract transit times are increased). The invention relates in particular to the treatment of such subjects.

BACKGROUND

Microbial overgrowth in the intestinal tract is closely associated with disorders which reduce intestinal motility in at least part of the intestinal tract and thus cause increased intestinal tract transit times. Such disorders include cystic fibrosis and other conditions arising from or associated with CFTR ion channel dysfunction (CFTR dysfunction) in the intestinal tract, liver and/or pancreas. This reduced motility, or even stasis (e.g. due to obstruction), of the intestinal contents allows microbes time to over-proliferate and have deleterious effects on the digestive processes of the subject. This reduced motility may also allow specific microbes to colonise inappropriately parts of the intestinal tract which are not their usual habitat, i.e. microbial overgrowth can occur when certain strains of microorganism grow in atypical parts of (or locations in) the intestinal tract. This inappropriate colonisation (growth in an atypical location) in turn can have deleterious effects on the digestive processes of the subject. As such, the effects of alginate oligomers in reducing increased transit times or preventing an increased transit time are expected to treat or prevent microbial overgrowth in the intestinal tract, especially in subjects with intestinal motility disorders, more especially subjects with reduced intestinal motility (i.e. where intestinal tract transit times are increased). In particular embodiments the invention relates to the use of alginate oligomers in the treatment or prevention of SIBO associated with cystic fibrosis and other conditions arising from or associated with CFTR dysfunction in the intestinal tract.

The gastrointestinal (GI) tract of vertebrates, also referred to as the digestive tract or alimentary canal, is the continuous series of organs beginning at the mouth and ending at the anus. Specifically, this sequence consists of the mouth, the pharynx, the oesophagus, the stomach (or stomachs in ruminant mammals), the duodenum, the small intestine, the large intestine and the anus. For the purposes of this invention, these organs can be subdivided into the upper GI tract, consisting of the mouth, pharynx, oesophagus, and stomach(s), and the lower GI tract (the intestinal tract), consisting of the duodenum, the jejunum, the ileum (together the small intestine), the cecum, the colon, the rectum (together the large intestine) and the anus.

The GI tract, and the intestinal tract in particular, is colonised by microbes, especially bacteria. These microbes are an essential part of the digestive system of the vertebrate host, assisting in the breakdown of dietary molecules into absorbable components. It is become increasing clear that these microbes also contribute to the correct functioning of diverse physiological systems beyond the digestive system.

However, it is also becoming clear that when the overall numbers of the intestinal microbiota become too high, or more specifically there is growth of a particular strain at an atypical location in the intestinal tract (inappropriate colonisation), this can have detrimental effects on the subject's digestive processes causing, for example, loss of appetite, nausea, flatulence, diarrhoea, constipation, abdominal distension, abdominal pain sensations of bloating, steatorrhea, weight loss, fatigue, vitamin and/or mineral deficiencies (e.g. deficiencies in vitamins A, D, E, K and B12, and iron), folate excess, hypoproteinemia, hypoalbuminemia, decreased xylose absorption, anaemia, osteoporosis and malnourishment. In chronic cases the metabolic products of the microbes can lead to damage to the subject's intestinal tissues and wider toxicity.

The intestinal microbiota can reach these levels, or grow in atypical locations, when a subject's intestinal transit times are increased in at least a part of the intestinal tract or in the extreme where there is stasis of the luminal contents (e.g. due to obstruction). Problems with intestinal motility may result from problems caused by the physical nature of the organs and their contents (viscous mucus, obstruction, narrowed lumen) or from problems caused by the control exerted by the nervous system on the peristaltic action of the intestines. As such, intestinal motility problems are commonly seen in subjects suffering from cystic fibrosis and other conditions arising from or associated with CFTR dysfunction in the intestinal tract, scleroderma, celiac disease, inflammatory bowel disease (IBD) and its subtypes Crohn's disease and ulcerative colitis, and diabetes mellitus type 1 and type 2.

It is also understood that the levels of intestinal microbiota are controlled to an extent by gastric secretions, pancreatic secretions and bile. Pancreatic and bile secretions are often reduced in subjects with conditions arising from or associated with CFTR dysfunction, e.g. cystic fibrosis, on account of the blockage of the secretory ducts with the abnormal mucus associated with CFTR dysfunction and/or because the secretions themselves are abnormally viscous. Consequently, subjects with conditions arising from or associated with CFTR dysfunction in the pancreas and/or liver as well as the intestinal tract are especially susceptible to intestinal microbial overgrowth.

Alginate oligomers have been described in the literature at length. Briefly, alginates are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate). Alginate oligomers may be obtained from alginate polymers which are typically isolated from natural sources as large high molecular weight polymers (e.g. an average molecular weight in the range 300,000 to 500,000 Daltons). Such large alginate polymers may be degraded, or broken down, e.g. by chemical or enzymatic hydrolysis to produce alginate structures of lower molecular weight.

SUMMARY

It has now been found that alginate oligomers may act to decrease intestinal tract transit times, including in subjects with intestinal motility disorders, especially subjects with reduced intestinal motility. Alginate oligomers may therefore be considered to act to increase intestinal motility, and as such would be useful in the treatment or prevention of microbial overgrowth in the intestinal tract including in subjects with intestinal motility disorders, especially subjects with reduced intestinal motility (i.e. where intestinal tract transit times are increased). The antimicrobial properties of alginate oligomers may also contribute to the beneficial effects of alginate oligomers in such subjects.

Thus, in one aspect the invention provides a method for the treatment or prevention of microbial overgrowth in at least part of the intestinal tract of a subject, said method comprising administering an effective amount of an alginate oligomer to a subject in need thereof.

Expressed alternatively, the invention provides an alginate oligomer for use in the treatment or prevention of microbial overgrowth in at least part of the intestinal tract of a subject.

Expressed alternatively again, the invention provides the use of an alginate oligomer in the manufacture of a medicament for use in the treatment or prevention of microbial overgrowth in at least part of the intestinal tract a subject.

The invention further provides a pharmaceutical composition for said uses and for use in said method (and the other methods and uses described herein), said composition comprising an alginate oligomer and a pharmaceutically acceptable excipient, carrier or diluent, e.g. those described below.

References to the intestinal tract include any part of the lower GI tract, e.g. the small intestine (the duodenum, the jejunum and the ileum), the large intestine (the cecum, the colon and the rectum) and the anus or any part thereof.

In certain embodiments it is microbial overgrowth in at least part of the small intestine which is treated or prevented in accordance with the invention. In these embodiments the invention may be expressed as a method for the treatment or prevention of small intestinal microbial overgrowth in a subject, said method comprising administering an effective amount of an alginate oligomer to a subject in need thereof.

Expressed alternatively, the invention provides an alginate oligomer for use in the treatment or prevention of small intestinal microbial overgrowth in a subject.

Expressed alternatively again, the invention provides the use of an alginate oligomer in the manufacture of a medicament for use in the treatment or prevention of small intestinal microbial overgrowth in a subject.

DETAILED DESCRIPTION

References to small intestinal microbial overgrowth, include small intestinal bacterial overgrowth (SIBO), blind loop syndrome (BLS) and bacterial overgrowth syndrome (BOS).

Administering the alginate oligomer to the subject preferably results in the at least part of the intestinal tract having microbial overgrowth or being at risk thereof being contacted with an alginate oligomer in an amount effective to (or sufficient to) treat or prevent the microbial overgrowth. In particular, the step of administering the alginate oligomer to a subject, and in particular to a subject in need of such treatment (e.g. a subject having, suspected to have, or being at risk of microbial overgrowth in at least part of their intestinal tract) may be by any means of delivering the alginate oligomer to the microbes of the overgrowth or the at least part of the intestinal tract having or being at risk of microbial overgrowth, whether directly or indirectly, e.g. by administering the alginate oligomer orally, rectally, intravenously, intra-arterially or intraintestinally.

The amount of alginate oligomer effective to (or sufficient to) treat or prevent intestinal microbial overgrowth may be an amount effective or sufficient to reduce, or prevent from increasing, the time luminal contents take to transit the at least part of the intestinal tract having microbial overgrowth or being at risk thereof, or the entire length of the intestinal tract, or small intestine or large intestine (as appropriate). This may be considered to be an amount effective or sufficient to enhance or maintain intestinal (luminal) motility in the at least part of the intestinal tract having microbial overgrowth or being at risk thereof, or the entire length of the intestinal tract, or small intestine or large intestine (as appropriate). The skilled practitioner would be able to monitor transit times and/or intestinal (luminal) motility in the subject undergoing the methods of the invention.

Thus, the methods and uses of the invention may be considered to be methods or uses for reducing intestinal transit time in a subject, or for reducing an increase in intestinal transit time. More particularly, the methods or uses of the invention may be seen as methods or uses wherein the time luminal contents take to transit the at least part of the intestinal tract having microbial overgrowth or being at risk thereof is reduced or prevented from increasing. The methods and uses of the invention may also be considered to be methods or uses wherein intestinal (luminal) motility in the at least part of the intestinal tract having microbial overgrowth or being at risk thereof is enhanced or prevented from decreasing. In some embodiments this may be methods or uses wherein obstruction of the lumen at the at least part of the intestinal tract having microbial overgrowth or being at risk thereof is delayed, reduced, limited, or prevented. Thus included is absolute prevention of an obstruction and any delay in the onset or development of the obstruction, or reduction or limitation on the development or progression of the obstruction.

In other embodiments the method or uses of the invention may treat or prevent microbial overgrowth in at least part of the intestinal tract of a subject in which intestinal tract transit time and/or intestinal motility is essentially normal, i.e. the subject shows no apparent reduction in intestinal tract transit time and/or intestinal motility. These may be subjects with reduced pancreatic and bile secretions, e.g. subjects with conditions arising from or associated with CFTR dysfunction, e.g. cystic fibrosis, i.e. subjects whose pancreatic and bile secretions are insufficient to control levels of intestinal microbiota.

The microbial overgrowth may contain any microbial cellular organism (which term is interchangeable with "cellular microorganism"); that is any cellular organism that is microscopic, namely too small to be seen by the naked eye. In particular as used herein the term includes the organisms typically thought of as microorganisms, particularly bacteria, fungi, archaea, algae and protists. The microorganism may be prokaryotic or eukaryotic, and may be from any class, genus or species of microorganism. The microorganism may be aerobic or anaerobic. The microorganism may be pathogenic or non-pathogenic, or may be a spoilage or an indicator microorganism.

Bacteria represent the most commonly encountered constituents of intestinal microbial overgrowths. The bacteria in an overgrowth may be selected from the following genera: *Achromobacter, Acinetobacter, Actinobacillus, Aeromonas, Agrobacterium, Alcaligenes, Alteromonas, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Escherichia, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces, Treponem* and *Yersinia*.

Thus, the bacteria may be Gram-positive or Gram-negative bacteria, or indeed Gram-indeterminate bacteria. Gram-negative bacteria are of importance. Within the Gram-negative bacteria the Enterobacteriaceae and the Gram-negative bacteria non-fermenting bacteria are of particular note.

Enterobacteriaceae include, but are not limited to, bacteria from the genera *Alishewanella, Alterococcus, Aquamonas, Aranicola, Azotivirga, Brenneria, Budvicia, Buttiauxella, Cedecea, Citrobacter, Cronobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Phlomobacter, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia, Yokenella*. In accordance with the invention important genera of Enterobacteriaceae include *Escherichia, Klebsiella, Salmonella, Shigella*, and *Yersinia* and *Providencia*.

Non-fermenting Gram-negative bacteria include, but are not limited to, bacteria from the genera *Pseudomonas, Acinetobacter, Stenotrophomonas* and *Burkholderia, Achromobacter, Algaligenes, Bordetella, Brevundimonas, Comamonas, Elizabethkingia* (formerly *Chryseobacterium*), *Methylobacterium, Moraxella, Ochrobactrum, Oligella, Psychrobacter, Ralstonia, Roseomonas, Shewanella, Sphingobacterium*, e.g. *Pseudomonas aeruginosa, Acinetobacter baumannii, Stenotrophomonas maltophilia*, and *Burkholderia* spp.

Particularly important bacteria in accordance with the invention include, but are not limited to, *Escherichia coli, Streptococcus, Lactobacillus, Bacteroides*, and *Enterococcus* species.

The amount of microbes found in the luminal contents of the intestinal tract varies over the course of the intestinal tract. Overgrowth may therefore be broadly defined as an overall (or total) amount of microbes in the luminal contents of a selected part of a subject's intestinal tract that is increased compared to normal amounts in said subject. That is, increased sufficiently to result in one or more symptoms of intestinal microbial overgrowth.

The profile of the constituent strains of the intestinal microbiota also varies over the course of the intestinal tract. In these more specific contexts overgrowth may be defined as growth of one or more strains of microorganism at an atypical part (location) in the intestinal tract (i.e. inappropriate colonisation of at least part of the intestinal tract by one or more strains of microorganism). That is, a level of growth at an atypical location/inappropriate colonisation sufficient to result in one or more symptoms of intestinal microbial overgrowth.

Expressed numerically, microbial overgrowth may be defined as an amount of microbes in a unit volume or weight of the luminal contents of a selected part of a subject's intestinal tract (e.g. 1 ml or 1 g) that is at least about 10 times, e.g. at least about 20, 30, 40, 50, 60, 70, 80, 90 or 100 times that compared to normal amounts in said subject. This may be in general terms the overall (or total) amount of microbes in the luminal contents or, more specifically, the amount of a specific strain or strains of microorganism. In other embodiments comparison may be made with an average, e.g. mean, of corresponding value(s) obtained from the same part of the intestinal tracts of a plurality of healthy subjects.

More specifically, microbial overgrowth in the small intestine may be defined as a microbial population in the small intestine exceeding about $10^4$, e.g. exceeding about $5\times10^4$, $10^5$, $5\times10^4$, $10^6$, $5\times10^6$, or $10^7$ organisms/ml or g of luminal contents. Even more specifically microbial overgrowth in the small intestine may be defined as a microbial population in the ileum exceeding about $10^4$, e.g. exceeding about $5\times10^4$, $10^5$, $5\times10^4$, $10^6$, $5\times10^6$, or $10^7$ organisms/ml or g of luminal contents and/or a microbial population in the duodenum and/or the jejunum exceeding about $10^3$, e.g. exceeding about $5\times10^3$, $10^4$, $5\times10^4$, $10^5$, $5\times10^5$, or $10^6$ organisms/ml or g of luminal contents.

More specifically, microbial overgrowth in the large intestine may be defined as a microbial population in the large intestine exceeding about $10^{12}$, e.g. exceeding about $5\times10^{12}$, $10^{13}$, $5\times10^{13}$, $10^{14}$, $5\times10^{14}$, or $10^{15}$ organisms/ml or g of luminal contents. Even more specifically microbial overgrowth in the large intestine may be defined as a microbial population in the colon and/or the rectum exceeding about $10^{12}$, e.g. exceeding about $5\times10^{12}$, $10^{13}$, $5\times10^{13}$, $10^{14}$, $5\times10^{14}$, or $10^{15}$ organisms/ml or g of luminal contents and/or a microbial population in the cecum exceeding about $10^6$, e.g. exceeding about $5\times10^6$, $10^7$, $5\times10^7$, $10^8$, $5\times10^8$, or $10^9$ organisms/ml or g of luminal contents.

Microbial counts may be performed by any convenient means on a sample collected from the luminal contents at the target part of the subject's intestinal tract, e.g. anaerobic and aerobic colony counts of luminal contents. In such embodiments the above reference to organisms/ml or g of luminal contents may be expressed as colony forming units per ml or g of luminal contents. In other embodiments fluorescence based cell counts may be made.

The symptoms of intestinal microbial overgrowth include loss of appetite, nausea, flatulence, diarrhoea, constipation, abdominal distension, abdominal pain sensations of bloating, steatorrhea, weight loss, fatigue, vitamin and/or mineral deficiencies (e.g. deficiencies in vitamins A, D, E, K and B12, and iron), folate excess, hypoproteinemia, hypoalbuminemia, decreased xylose absorption, anaemia, osteoporosis and malnourishment. In chronic cases the metabolic products of the microbes can lead to damage to the subjects intestinal tissues and wider toxicity. The skilled practitioner would be able to identify patterns of symptoms which would be indicative of, or attributable to, intestinal microbial overgrowth.

Diagnosis may also be via well-established breath tests based on bacterial metabolism of carbohydrates (e.g. glucose, D-xylose or lactulose) to hydrogen and/or methane or based on the bacterial metabolism of radiolabelled forms of the bile acid glycocholic acid to $CO_2$.

Diagnosis may also be via tests monitoring D-xylose levels in body fluids other than GI tract contents (e.g. blood or urine) following oral consumption of D-xylose. An absence of D-xylose in such body fluids in indicative of intestinal microbial overgrowth.

Diagnosis may also involve visual inspection of the intestines by endoscopy and/or biopsy. Blunting of villi, hyperplasia of crypts and an increased number of lymphocytes in the lamina propria are indicative of intestinal microbial overgrowth.

The subject may be a subject suffering from a condition arising from or associated with CFTR dysfunction in the intestinal tract, liver and/or pancreas, scleroderma, celiac disease, inflammatory bowel disease (IBD) and its subtypes Crohn's disease and ulcerative colitis, and diabetes mellitus type 1 and type 2.

A condition arising from, associated with, or characterised by defective CFTR ion channel function in the intestinal tract, liver and/or pancreas includes conditions arising from said defective CFTR ion channel function at these sites or complications thereof. A "defective CFTR ion channel" will be understood from the above to include any defect or deficiency in CFTR function, i.e. CFTR dysfunction. Thus "a defective CFTR ion channel" effectively means, and may alternatively be expressed as, "defective CFTR ion channel function". The condition may thus be viewed as a condition associated with or characterised by or arising from CFTR dysfunction in the intestinal tract, liver and/or pancreas. This may include CFTR ion channels which are defective in the sense that they are non-functional or have reduced function, i.e. partially or fully lack CFTR ion channel activity (in other words in which CFTR ion channel activity is reduced or abrogated).

Defective CFTR function may arise from genetic defect or mutation or may be acquired in any other way.

The most commonly known disease associated with defective CFTR function is cystic fibrosis (CF). CF is an autosomal recessive genetic disease of humans arising from mutations in the CFTR which result in stagnant mucus in all organs where mucus is formed and thickened secretions from glands in the liver and the pancreas. The presence of this stagnant mucus in the lungs, paranasal sinuses, GI tract, pancreas, liver and female and male reproductive systems leads to a plethora of clinical conditions associated not only with poor quality of life but also morbidity and mortality. Indeed, most CF sufferers succumb to a medical disorder or condition directly associated with this stagnant mucus In some instances CFTR dysfunction is seen in subjects that have non-compound heterozygous mutant CFTR alleles. In such subjects the inherited dysfunction is mild and so is insufficient to manifest as overt CF, but is sufficient to result in some or all of the plethora of clinical conditions and complications associated with overt CF, include those of the GI tract and the pancreas.

Acquired CFTR dysfunction may arise due to environmental and/or clinical exposure, e.g. through the chronic inhalation of particulate irritants, e.g. smoke particles (tobacco, wood etc.), pollution, dust (asbestos, cotton, coal, stone, animal droppings etc.) and spores.

The above discussed conditions associated with or characterised by defective CFTR ion channel function in the intestinal tract, liver and/or pancreas are described in greater detail in WO2015/128495, the contents of which are incorporated herein by reference.

In certain embodiments therefore the invention provides a method for the treatment or prevention of small intestinal bacterial overgrowth in a subject with a condition arising from, associated with, or characterised by defective CFTR ion channel function in the intestinal tract, liver and/or pancreas, preferably cystic fibrosis, said method comprising administering an effective amount of an alginate oligomer to said subject.

Expressed alternatively, the invention provides an alginate oligomer for use in the treatment or prevention of small intestinal bacterial overgrowth in a subject with a condition arising from, associated with, or characterised by defective CFTR ion channel function in the intestinal tract, liver and/or pancreas, preferably cystic fibrosis.

Expressed alternatively again, the invention provides the use of an alginate oligomer in the manufacture of a medicament for use in the treatment or prevention of small intestinal bacterial overgrowth in a subject with a condition arising from, associated with, or characterised by defective CFTR ion channel function in the intestinal tract, liver and/or pancreas, preferably cystic fibrosis.

In these embodiments the small intestinal bacterial overgrowth undergoing treatment in accordance with the invention may be termed (intestinal, hepatic and/or pancreatic) CFTR dysfunction associated SIBO, or more particularly, cystic fibrosis associated SIBO. These embodiments may of course be extended to microbial overgrowth in general and/or the intestinal tract in general.

In certain embodiments the methods of the invention will further comprise a preceding step in which it is determined that the subject has microbial overgrowth in at least part of their intestinal tract. This may be using the tests described above, e.g. microbial counts (of overall numbers or specific strains). In the more specific embodiments of said method said preceding step may determine that the subject has SIBO, e.g. CFTR dysfunction associated SIBO, or cystic fibrosis associated SIBO. In other embodiments the methods of the invention will further comprise a preceding step in which it is determined whether or not that the subject has increased intestinal transit time and/or decreased intestinal motility and/or an intestinal obstruction.

In other embodiments the methods of the invention will further comprise a following step in which the clinical indictors of the microbial overgrowth in at least part of the subject's intestinal tract, e.g. the symptoms and indicators described above and/or microbial counts, are assessed and preferably compared to a corresponding assessment made prior to, or earlier in, said treatment in order to determine any changes therein. In the more specific embodiments of said method said following step may assess the clinical indicators of SIBO, e.g. CFTR dysfunction associated SIBO, or cystic fibrosis associated SIBO. In other embodiments the methods of the invention will further comprise a following step in which it is determined whether or not treatment has increased intestinal transit time and/or decreased intestinal motility and/or reduced an intestinal obstruction. This may also or alternatively involve determining whether or not intestinal transit time has increased further and/or whether or not intestinal motility has decreased further or whether or not intestinal obstruction has increased (worsened)

As noted above, alginates typically occur as polymers of an average molecular mass of at least 35,000 Daltons, i.e. approximately 175 to approximately 190 monomer residues, although typically much higher and an alginate oligomer according to the present invention may be defined as a material obtained by fractionation (i.e. size reduction) of an alginate polymer, commonly a naturally occurring alginate. An alginate oligomer can be considered to be an alginate of an average molecular weight of less than 35,000 Daltons (i.e. less than approximately 190 or less than approximately 175 monomer residues), in particular an alginate of an average molecular weight of less than 30,000 Daltons (i.e. less than approximately 175 or less than approximately 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more units or residues and an alginate oligomer for use according to the invention will typically contain 2 to 100 monomer residues, more typically 3, 4, 5 or 6 to 100, and may contain 2, 3, 4, 5 or 6 to 75, 2, 3, 4, 5 or 6 to 50, 2, 3, 4, 5 or 6 to 40, 2, 3, 4, 5 or 6 to 35 or 2, 3, 4, 5 or 6 to 30 residues. Thus, an alginate oligomer for use according to the invention will typically have an average molecular weight of 350, 550, 700, 900 or 1000 to 20,000 Daltons, 350, 550, 700, 900 or 1000 to 15,000 Daltons, 350, 550, 700, 900 or 1000 to 10,000 Daltons, 350, 550, 700, 900 or 1000 to 8000 Daltons, 350, 550, 700, 900 or 1000 to 7000 Daltons, or 350, 550, 700, 900 or 1000 to 6,000 Daltons.

Alternatively put, the alginate oligomer may have a degree of polymerisation (DP), or a number average degree of polymerisation (DPn) of 2 to 100, preferably 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include any one of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

The alginate oligomer is preferably a linear oligomer.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include alginate oligomers with (e.g. containing) 30 to 70% G (guluronate) residues or 70 to 100% G (guluronate) residues. Thus, a representative alginate oligomer for use according to the present invention may contain at least 70% G residues (i.e. at least 70% of the monomer residues of the alginate oligomer will be G residues).

Preferably at least 50% or 60%, more particularly at least 70% or 75%, even more particularly at least 80, 85, 90, 91, 92, 93, 94, 95, 96, 97, 98 or 99% of the monomer residues are guluronate. In one embodiment the alginate oligomer may be an oligoguluronate (i.e. a homooligomer of G, or 100% G).

In a further preferred embodiment, the above described alginates of the invention have a primary structure wherein the majority of the G residues are in so called G-blocks. Preferably at least 50%, more preferably at least 70 or 75%, and most preferably at least 80, 85, 90, 92 or 95% of the G residues are in G-blocks. A G block is a contiguous sequence of at least two G residues, preferably at least 3 contiguous G residues, more preferably at least 4 or 5 contiguous G residues, most preferably at least 7 contiguous G residues.

In particular at least 90% of the G residues are linked 1-4 to another G residue. More particularly at least 95%, more preferably at least 98%, and most preferably at least 99% of the G residues of the alginate are linked 1-4 to another G residue.

The alginate oligomer of use in the invention is preferably a 3- to 35-mer, more preferably a 3- to 28-mer, in particular a 4- to 25-mer, e.g. a 5- to 20-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons or 2000 to 3000 Daltons or 900 to 3500 Daltons. Other representative alginate oligomers include, as mentioned above, oligomers with 5, 6, 7, 8, 9, 10, 11, 12 or 13 to 50, 45, 40, 35, 28, 25, 22 or 20 residues.

It may be a single compound or it may be a mixture of compounds, e.g. of a range of degrees of polymerization. As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

The alginate oligomer of the invention may have a degree of polymerisation (DP), or a number average degree of polymerisation ($DP_n$), of 3-28, 4-25, 6-22, 8-20 or 10-15, or 5-18 or 7-15 or 8-12, especially 10.

The alginate oligomer of the invention may have a degree of polymerisation (DP), or a number average degree of polymerisation ($DP_n$), of 3-24, 4-23, 5-22, 6-21, 7-20, 8-19, 9-18, 10-17, 11-16, 12-15 or 13-14 (e.g. 13 or 14).

The alginate oligomer of the invention may have a degree of polymerisation (DP), or a number average degree of polymerisation (DPn), of 4-25, 5-24, 6-23, 7-22, 8-21, 9-20, 10-19, 11-18, 12-17, 13-16, 14-15 (e.g. 14 or 15).

The alginate oligomer of the invention may have a degree of polymerisation (DP), or a number average degree of polymerisation ($DP_n$), of 5-26, 6-25, 7-24, 8-23, 9-22, 10-21, 11-20, 12-19, 13-18, 14-17 or 15-16 (e.g. 15 or 16).

The alginate oligomer of the invention may have a degree of polymerisation (DP), or a number average degree of polymerisation ($DP_n$), of 4-50, 4-40, 4-35, 4-30, 4-28, 4-26, 4-22, 4-20, 4-18, 4-16 or 4-14.

The alginate oligomer of the invention may have a degree of polymerisation (DP), or a number average degree of polymerisation ($DP_n$), of 5-50, 5-40, 5-25, 5-22, 5-20, 5-18, 5-23, 5-20, 5-18, 5-16 or 5-14.

The alginate oligomer of the invention may have a degree of polymerisation (DP), or a number average degree of polymerisation ($DP_n$), of 6-50, 6-40, 6-35, 6-30, 6-28, 6-26, 6-24, 6-20, 6-19, 6-18, 6-16 or 6-14.

The alginate oligomer of the invention may have a degree of polymerisation (DP), or a number average degree of polymerisation ($DP_n$), of 8-50, 8-40, 8-35, 8-30, 8-28, 8-25, 8-22, 8-20, 8-18, 8-16 or 8-14.

The alginate oligomer of the invention may have a degree of polymerisation (DP), or a number average degree of polymerisation ($DP_n$), of 9-50, 9-40, 9-35, 9-30, 9-28, 9-25, 9-22, 9-20, 9-18, 9-16 or 9-14.

The alginate oligomer of the invention may have a degree of polymerisation (DP), or a number average degree of polymerisation ($DP_n$), of 10-50, 10-40, 10-35, 10-30, 10-28, 10-25, 10-22, 10-20, 10-18, 10-16 or 10-14.

The alginate oligomer of the invention may have a degree of polymerisation (DP), or a number average degree of polymerisation ($DP_n$), of 11-50, 11-40, 11-35, 11-30, 11-28, 11-25, 11-22, 11-20, 11-18, 11-16 or 11-14.

The alginate oligomer of the invention may have a degree of polymerisation (DP), or a number average degree of polymerisation ($DP_n$), of 12-50, 12-40, 12-35, 12-30, 12-28, 12-25, 12-22, 12-20, 12-18, 12-16 or 12-14.

The alginate oligomer of the invention may have a degree of polymerisation (DP), or a number average degree of polymerisation ($DP_n$), of 13-50, 13-40, 13-35, 13-30, 13-28, 13-25, 13-22, 13-20, 13-18, 13-16 or 13-14 (e.g. 13 or 14).

The alginate oligomer of the invention may have a degree of polymerisation (DP), or a number average degree of polymerisation ($DP_n$), of 14-50, 14-40, 14-35, 14-30, 14-28, 14-25, 14-22, 14-20, 14-18, or 14-16.

The alginate oligomer of the invention may have a degree of polymerisation (DP), or a number average degree of polymerisation ($DP_n$), of 15-50, 15-40, 15-35, 15-30, 15-28, 15-25, 15-22, 15-20, or 15-18.

The alginate oligomer of the invention may have a degree of polymerisation (DP), or a number average degree of polymerisation ($DP_n$), of 18-50, 18-40, 18-35, 18-30, 18-28, 18-25, 18-22 or 18-20.

Preferably the alginate oligomer of the invention is substantially free, preferably essentially free, of alginate oligomers having a degree of polymerisation outside of the ranges disclosed herein. This may be expressed in terms of the molecular weight distribution of the alginate oligomer of the invention, e.g. the percentage of each mole of the alginate oligomer being used in accordance with the invention which has a DP outside the relevant range. The molecular weight distribution is preferably such that no more than 10%, preferably no more than 9, 8, 7, 6, 5, 4, 3, 2, or 1% mole has a DP of three, two or one higher than the relevant upper limit for $DP_n$. Likewise it is preferred that no more than 10%, preferably no more than 9, 8, 7, 6, 5, 4, 3, 2, or 1% mole has a DP below a number three, two or one smaller than the relevant lower limit for $DP_n$.

Suitable alginate oligomers are described in WO2007/039754, WO2007/039760, WO 2008/125828, and WO2009/068841, the disclosures of which are explicitly incorporated by reference herein in their entirety.

Representative suitable alginate oligomers have a $DP_n$ in the range 5 to 30, a guluronate fraction ($F_G$) of at least 0.80, a mannuronate fraction ($F_M$) of no more than 0.20, and at least 95 mole % of DP no more than 25.

Further suitable alginate oligomers have a number average degree of polymerization in the range 7 to 15 (preferably 8 to 12), a guluronate fraction ($F_G$) of at least 0.85 (preferably at least 0.90), a mannuronate fraction ($F_M$) of no more than 0.15 (preferably no more than 0.10), and having at least 95% mole with a degree of polymerization less than 17 (preferably less than 14).

Further suitable alginate oligomers have a number average degree of polymerization in the range 5 to 18 (especially 7 to 15), a guluronate fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17).

Further suitable alginate oligomers have a number average degree of polymerization in the range 5 to 18, a guluronate fraction ($F_G$) of at least 0.92, a mannuronate fraction ($F_M$) of no more than 0.08, and having at least 95% mole with a degree of polymerization less than 20.

Further suitable alginate oligomers have a number average degree of polymerization in the range 5 to 18 (preferably 7 to 15, more preferably 8 to 12, especially about 10), a guluronate fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14).

Further suitable alginate oligomers have a number average degree of polymerization in the range 7 to 15 (preferably 8 to 12), a guluronate fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Further suitable alginate oligomers have a number average degree of polymerization in the range 5 to 18, a guluronate fraction ($F_G$) of at least 0.80, a mannuronate fraction ($F_M$) of no more than 0.20, and having at least 95% mole with a degree of polymerization less than 20.

Further suitable alginate oligomers have a number average degree of polymerization in the range 7 to 15, a guluronate fraction ($F_G$) of at least 0.85, a mannuronate fraction ($F_M$) of no more than 0.15, and having at least 95% mole with a degree of polymerization less than 17.

Further suitable alginate oligomers have a number average degree of polymerization in the range 7 to 15, a guluronate fraction ($F_G$) of at least 0.92, a mannuronate fraction ($F_M$) of no more than 0.08, and having at least 95% mole with a degree of polymerization less than 17.

Further suitable alginate oligomers have a number average degree of polymerization in the range 5 to 20, a guluronate fraction ($F_G$) of at least 0.85 and a mannuronate fraction ($F_M$) of no more than 0.15.

Further suitable alginate oligomers have a number average degree of polymerization in the range 5 to 20, a guluronate fraction ($F_G$) of 0.9-0.95 and a mannuronate fraction ($F_M$) of 0.05-0.1, which may be expressed as an alginate oligomer having 90-95% G residues and an average molecular weight of 2600 Da. Further suitable alginate oligomers have a number average degree of polymerization about 13 (e.g. 12, 13 or 14), a guluronate fraction ($F_G$) of at least about 0.80, 0.85, 0.87, 0.88, 0.90 or 0.93 (e.g. 0.92, 0.93 or 0.94) and a corresponding mannuronate fraction ($F_M$) of no more than about 0.20, 0.15, 0.13, 0.12, 0.10, or 0.07 (e.g. 0.08, 0.07 or 0.06).

Further suitable alginate oligomers have a number average degree of polymerization about 21 (e.g. 20, 21 or 22), a guluronate fraction ($F_G$) of at least about 0.80 (e.g. 0.85, 0.87, 0.88, 0.90, 0.92, 0.94 or 0.95) and a corresponding mannuronate fraction ($F_M$) of no more than about 0.20 (e.g. 0.15, 0.13, 0.12, 0.10, 0.08, 0.06, 0.05).

Further suitable alginate oligomers have a number average degree of polymerization about 6 (e.g. 5, 6 or 7), a guluronate fraction ($F_G$) of at least about 0.80 (e.g. 0.85, 0.87, 0.88, 0.90, 0.92, 0.94 or 0.95) and a corresponding mannuronate fraction ($F_M$) of no more than about 0.20 (e.g. 0.15, 0.13, 0.12, 0.10, 0.08, 0.06, 0.05).

It will thus be seen that a particular class of alginate oligomers favoured according to the present invention is alginate oligomers defined as so-called "high G" or "G-block" oligomers i.e. having a high content of G residues or G-blocks (e.g. wherein at least 70% of the monomer residues are G, preferably arranged in G-blocks). However, other types of alginate oligomer may also be used, including in particular "high M" or "M-block" oligomers or MG-block oligomers, as described further below. Accordingly, it is alginate oligomers with high proportions of a single monomer type, and with said monomers of this type being present predominantly in contiguous sequences of that monomer type, that represent oligomers that are particularly preferred, e.g. oligomers wherein at least 70% of the monomer residues in the oligomer are G residues linked 1-4 to another G-residue, or more preferably at least 75%, and most preferably at least 80, 85, 90, 92, 93, 94, 95, 96, 97, 98, 99% of the monomers residues of the oligomer are G residues linked 1-4 to another G residue. This 1-4 linkage of two G residues can be alternatively expressed as a guluronic unit bound to an adjacent guluronic unit.

In a further embodiment at least, or more particularly more than, 50% of the monomer residues of the alginate oligomer may be M residues (i.e. mannuronate or mannuronic acid). In other words the alginate oligomer will contain at least or alternatively more than 50% mannuronate (or mannuronic acid) residues. Specific embodiments thus include alginate oligomers with (e.g. containing) 50 to 70% M (mannuronate) residues or e.g. 70 to 100% M (mannuronate) residues. Further specific embodiments also include oligomers containing 71 to 85% M residues or 85 to 100% M residues. Thus, a representative alginate oligomer for use according to this embodiment of the present invention will contain more than 70% M residues (i.e. more than 70% of the monomer residues of the alginate oligomer will be M residues).

In other embodiments at least 50% or 60%, more particularly at least 70% or 75%, even more particularly at least 80, 85, 90, 95 or 99% of the monomer residues are mannuronate. In one embodiment the alginate oligomer may be an oligomannuronate (i.e. a homooligomer of M, or 100% M).

In a further embodiment, the above described alginates of the invention have a primary structure wherein the majority of the M residues are in so called M-blocks. In this embodiment preferably at least 50%, more preferably at least 70 or 75%, and most preferably at least 80, 85, 90 or 95% of the M residues are in M-blocks. An M block is a contiguous sequence of at least two M residues, preferably at least 3 contiguous M residues, more preferably at least 4 or 5 contiguous M residues, most preferably at least 7 contiguous M residues.

In particular, at least 90% of the M residues are linked 1-4 to another M residue. More particularly at least 95%, more preferably at least 98%, and most preferably at least 99% of the M residues of the alginate are linked 1-4 to another M residue.

Other preferred oligomers are alginate oligomers wherein at least 70% of the monomer residues in the oligomer are M residues linked 1-4 to another M-residue, or more preferably at least 75%, and most preferably at least 80, 85, 90, 92, 93, 94, 95, 96, 97, 98, 99% of the monomers residues of the oligomer are M residues linked 1-4 to another M residue. This 1-4 linkage of two M residues can be alternatively expressed as a mannuronic unit bound to an adjacent mannuronic unit.

In a still further embodiment, the alginate oligomers of the invention comprise a sequence of alternating M and G residues. A sequence of at least three, preferably at least four, alternating M and G residues represents an MG block. Preferably the alginate oligomers of the invention comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue. Preferably the MG block is at least 5 or 6 contiguous residues, more preferably at least 7 or 8 contiguous residues.

In a further embodiment the minority uronate in the alginate oligomer (i.e. mannuronate or guluronate) is found predominantly in MG blocks. In this embodiment preferably at least 50%, more preferably at least 70 or 75% and most preferably at least 80, 85, 90 or 95% of the minority uronate monomers in the MG block alginate oligomer are present in MG blocks. In another embodiment the alginate oligomer is arranged such that at least 50%, at least 60%, at least 70%, at least 80%, at least 85%, at least 90%, at least 95%, at least 99%, e.g. 100% of the G and M residues in the oligomer are arranged in MG blocks.

Although at its broadest, the invention extends to embodiments wherein at least 1% but less than 100% of the monomer residues of the oligomer are G residues (i.e. guluronate or guluronic acid), more particularly, and as defined further below, at least 30% of the monomer residues are G residues. Thus, at its broadest the MG block containing alginate oligomer may contain at least 1%, but less than 100%, guluronate (or guluronic acid) residues, but generally the MG block containing alginate oligomer will contain at least 30% (or at least 35, 40 or 45% or 50% G) but less than 100% G. Specific embodiments thus include MG block containing alginate oligomers with (e.g. containing) 1 to 30% G (guluronate) residues, 30 to 70% G (guluronate) residues or 70 to 99% G (guluronate) residues. Thus, a representative MG block containing alginate oligomer for use according to the present invention may contain more than 30%, but less than 70%, G residues (i.e. more than 30%, but less than 70%, of the monomer residues of the MG block alginate oligomer will be G residues).

Preferably more than 30%, more particularly more than 35% or 40%, even more particularly more than 45, 50, 55, 60 or 65%, but in each case less than 70%, of the monomer residues of the MG block containing alginate oligomer are guluronate. Alternatively, less than 70%, more preferably less than 65% or 60%, even more preferably less than 55, 50, 45, 40 or 35%, but in each case more than 30% of the monomer residues of the MG block containing alginate oligomer are guluronate. Any range formed by any combination of these values may be chosen. Therefore for instance the MG block containing alginate oligomer can have e.g. between 35% and 65%, 40% and 60% or 45% and 55% G residues.

In another embodiment the MG block containing alginate oligomer may have approximately equal amounts of G and M residues (e.g. ratios between 65% G/35% M and 35% G/65% M, for instance 60% G/40% M and 40% G/60% M; 55% G/45% M and 45% G/55% M; 53% G/47% M and 47% G/53% M; 51% G/49% M and 49% G/51% M; e.g. about 50% G and about 50% M) and these residues are arranged predominantly, preferably entirely or as completely as possible, in an alternating MG pattern (e.g. at least 50% or at least 60, 70, 80, 85, 90 or 95% or 100% of the M and G residues are in an alternating MG sequence).

In certain embodiments the terminal uronic acid residues of the alginate oligomers of use in the invention do not have a double bond, especially a double bond situated between the $C_4$ and $C_5$ atom. Such oligomers may be described as having saturated terminal uronic acid residues or as being saturated alginate oligomers. The skilled man would be able to prepare oligomers with saturated terminal uronic acid residues without undue burden. This may be through the use of production techniques which yield such oligomers, or by converting (saturating) oligomers produced by processes that yield oligomers with unsaturated terminal uronic acid residues.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion (e.g. digestion with an alginate lyase (e.g. enzymes within EC 4.2.2.3 and/or EC 4.2.2.11)) and/or acid hydrolysis. In one favoured embodiment acid hydrolysis (of alginate polysaccharides) is used to prepare the alginate oligomers of the invention. In other embodiments enzymatic digestion (of alginate polysaccharides), in particular digestion with an alginate lyase, is used with an additional processing step(s) to saturate the terminal uronic acids in the oligomers.

Oligomers may then be separated from the polysaccharide breakdown products chromatographically using an ion exchange resin or by fractionated precipitation or solubilisation or filtration. U.S. Pat. No. 6,121,441 and WO 2008/125828, which are explicitly incorporated by reference herein in their entirety, describe a process suitable for preparing the alginate oligomers of use in the invention. Further information and discussion can be found in for example in "Handbooks of Hydrocolloids", Ed. Phillips and Williams, CRC, Boca Raton, Fla., USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from, but not limited to, *Laminaria hyperbora* and *Lessonia nigrescens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii*.

In embodiments where alginate oligomers which have primary structures in which the majority of the G residues are arranged in G-blocks rather than as single residues are required, algal sources are expected to be most suitable on account of the fact that the alginates produced in these organisms tend to have these structures. The bacterial sources may be more suitable for obtaining alginate oligomers of different structures.

The molecular apparatus involved in alginate biosynthesis in *Pseudomonas fluorescens* and *Azotobacter vinelandii* has been cloned and characterised (WO 94/09124; Ertesvag, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al, Journal of Bacteriology, 2006, Vol 188(15), 5551-5560) and alginates of tailored primary structures can be readily obtained by manipulating these systems.

The G content of alginates (for example an algal source material) can be increased by epimerisation, for example with mannuronan C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azotobacter vinelandii* AlgE epimerases is described in detail in Ertesvåg et al (supra) and Strugala et al (Gums and Stabilisers for the Food Industry, 2004, 12, The Royal Society of Chemistry, 84-94).

To obtain G-block containing alginates or alginate oligomers, epimerisation with one or more *Azotobacter vinelandii* AlgE epimerases other than AlgE4 is preferred as these enzymes are capable of producing G block structures. On the other hand AlgE4 epimerase can be used to create alginates or alginate oligomers with alternating stretches of M/G sequence or primary structures containing single G residue as it has been found that this enzyme seems preferentially to epimerise individual M residues so as to produce single G residues linked to M residues rather than producing G blocks. Particular primary structures can be obtained by using different combinations of these enzymes.

Mutated versions of these enzymes or homologues from other organisms are also specifically contemplated as of use. WO 94/09124 describes recombinant or modified mannuronan C-5 epimerase enzymes (AlgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AlgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure for subsequent alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AlgE genes is disclosed in Gimmestad, M., et al, 2006 (supra).

A further approach is to delete or inactivate the endogenous epimerase genes from an *Azotobacter* or a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer products can be influenced by the culture conditions. It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in a capacity to treat or prevent microbial overgrowth in at least part of the intestinal tract of a subject that is substantially lower than that of the unmodified oligomer. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). The skilled man would be aware of still further chemical modifications that can be made to the monosaccharide subunits of oligosaccharides and these can be applied to the alginate oligomers of the invention.

The invention encompasses the use of a single alginate oligomer or a mixture (multiplicity/plurality) of different alginate oligomers. Thus, for example, a combination of different alginate oligomers (e.g. two or more) may be used.

The subject may be any human or non-human animal subject, but more particularly may be a human or a non-human vertebrate, e.g. a non-human mammal, bird, amphibian, fish or reptile. In a preferred embodiment the subject is a mammalian subject. The animal may be a livestock or a domestic animal or an animal of commercial value, including laboratory animals or an animal in a zoo or game park. Representative animals therefore include dogs, cats, rabbits, mice, guinea pigs, hamsters, horses, pigs, sheep, goats and cows. Veterinary uses of the invention are thus covered. The subject may be viewed as a patient. Preferably the subject is a human. In some embodiments the subject is not a ruminant mammal.

"Treatment" when used in relation to the treatment of intestinal microbial overgrowth in a subject in accordance with the invention is used broadly herein to include any therapeutic effect, i.e. any beneficial effect on the condition or in relation to any symptom or sign associated with the condition (e.g. microbial counts). Thus, not only included is eradication or elimination of the overgrowth or any symptom or sign associated with the condition, or cure of the subject or condition (i.e. an essentially complete normalisation of the microbiota in the at least part of the intestinal tract previously having microbial overgrowth), but also any improvement in the condition or the subject as a whole. Thus included for example, is an improvement in any symptom or sign of the condition or in any clinically accepted indicator of the condition (e.g. microbial counts). Treatment thus includes both curative and palliative therapy, e.g. of a pre-existing or diagnosed condition, i.e. a reactionary treatment.

"Prevention" as used herein refers to any prophylactic or preventative effect. It thus includes delaying, limiting, reducing or preventing intestinal microbial overgrowth or one or more symptoms or indications thereof and also delaying, limiting, reducing or preventing the onset of the condition, or one or more symptoms or indications thereof, for example relative to the condition or symptom or indication thereof prior to the prophylactic treatment. Prophylaxis thus explicitly includes both absolute prevention of occurrence or development of intestinal microbial overgrowth, or symptom or indication thereof, and any delay in the onset or development of the condition or symptom or indication, or reduction or limitation on the development or progression of the condition.

The alginate oligomers of the invention may be administered to the subject in any convenient form or by any convenient means in order to achieve effective amounts at the at least part of the intestinal tract which has microbial overgrowth, e.g. by enteral (e.g. oral, buccal, sublingual, rectal), parenteral (e.g. intravenous, intra-arterial or intraintestinal) or by inhalation (including nasal inhalation). Preferably the alginate will be administered by enteral routes, most preferably oral or rectal. Oral administration may be particularly advantageous.

The skilled man will be able to formulate the alginate oligomers of the invention into pharmaceutical compositions that are adapted for these routes of administration according to any of the conventional methods known in the art and widely described in the literature.

More specifically, the alginate oligomers of the invention may be incorporated, optionally together with other active agents (e.g. those discussed herein), with one or more conventional carriers, diluents and/or excipients, to produce conventional galenic preparations such as tablets, pills, granules (including enteric coated granules), powders (e.g. inhalable powders, including dry inhalable powders), lozenges, sachets, cachets, elixirs, suspensions, emulsions, solutions, syrups, aerosols (as a solid or in a liquid medium), sprays (e.g. nasal sprays), compositions for use in nebulisers, soft and hard gelatine capsules, suppositories, sterile injectable solutions, sterile packaged powders, and the like. Enteric coated solid or liquid compositions, e.g. enteric coated tablets and enteric coated granules (which may be provided in an enteric-coated capsule or in a non-enteric-coated capsule i.e. in which the coating may or may not be an enteric coating), sterile inhalable and sterile injectable compositions are all of particular note.

Examples of suitable carriers, excipients, and diluents are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, buffering agents, and the like.

Additional therapeutically active agents may also be included in the pharmaceutical compositions, as discussed below in relation to combination therapies in the context of intestinal overgrowth in general and in subjects with cystic fibrosis or other conditions arising from or associated with CTFR dysfunction in the intestinal tract, liver and/or pancreas.

Parenterally administrable forms, e.g. solutions suitable for delivery via the intravenous, intra-arterial and intraintestinal routes mentioned above, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as sterile water for injection, Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975)), which is explicitly incorporated by reference herein in its entirety. The solutions can contain preservatives, antimicrobial agents, buffers and antioxidants conventionally used for parenteral solutions, excipients and other additives which are compatible with the biopolymers and which will not interfere with the manufacture, storage or use of products.

Simple sterile solutions of alginate oligomers or simple sterile liquid compositions comprising alginate oligomers may be especially convenient for use during surgical procedures, for intravenous, intra-arterial and intraintestinal use and for delivery to the lungs, e.g. by nebuliser. Such formulations may consist of sterile water and the alginate oligomer.

In other embodiments the alginate oligomers may simply be administered in drinking water or another foodstuff.

Solid or liquid formulations of the alginate oligomer may be provided with an enteric coating that prevents degradation in the stomach and/or other parts of the upper GI tract but permits degradation in the lower GI tract, e.g. the small intestine. Such coatings are routinely prepared from polymers including fatty acids, waxes, shellac, plastics, and plant fibres. Specific examples thereof include but are not limited to methyl acrylate-methacrylic acid copolymers, methyl methacrylate-methacrylic acid copolymers, cellulose acetate succinate, hydroxypropyl methylcellulose phthalate, hydroxypropyl methylcellulose acetate succinate (hypromellose acetate succinate), polyvinyl acetate phthalate (PVAP), cellulose acetate trimellitate, and sodium alginate polymer. Enteric coated tablets and enteric coated granules (which may be provided in an enteric-coated capsule or in a non-enteric coated capsule) are of particular note. Enteric coated granules may be prepared in accordance with the teachings of WO 1989008448 and Al-Khedairy, E. B. H, 2006, Iraqi J. Pharm. Sci., Vol. 15 (1) 49, the contents of which are incorporated herein by reference, although the skilled person would be aware of further alternative techniques which may be used.

The alginate oligomer can be incorporated into transdermal patches and the like. Further systems that are envisaged to be suitable are in situ drug delivery systems, for example gels where solid, semi-solid, amorphous or liquid crystalline gel matrices are formed in situ and which may comprise the alginate oligomer (which may be any alginate oligomer as herein defined). Such matrices can conveniently be designed to control the release of the alginate oligomer from the matrix, e.g. release can be delayed and/or sustained over a chosen period of time. Such systems may form gels only upon contact with biological tissues or fluids, e.g. the mucosal surfaces of the intestinal tract. Typically the gels are bioadhesive and/or mucoadhesive. Delivery to any body site, e.g. the intestinal tract, that can retain or be adapted to retain the pre-gel composition can be targeted by such a delivery technique. Such systems are described in WO 2005/023176), which is explicitly incorporated by reference herein in its entirety.

The relative content of the alginate oligomer in the compositions of the invention can vary depending on the dosage required and the dosage regime being followed but will be sufficient to achieve an effective amount at the target treatment area, taking account of variables such as the physical size of the subject to be treated, the nature of the subject's particular ailments, and the precise location and identity of the target treatment area. The skilled man would know that the amounts of alginate can be reduced if a multiple dosing regime is followed or increased to minimise the number of administrations or applications.

The alginate oligomer may be used at a daily dose of 0.1 g to 10 g, e.g. 0.5 g to 5 g, 0.8 g to 3 g, 1 g to 2 g, e.g. about 2 g, which may be administered at one or more times per day (e.g. bis daily) and in one or more dosage forms or administration events (e.g. two tablets bis daily).

A representative tablet to be used to administer an alginate oligomer of the invention to the lower GI tract may contain up to 99%, up to 95%, 90%, 85% or 80%, e.g. 50 to 95%, 55 to 95%, 60 to 95%, 65 to 95%, 70 to 95%, 75 to 95%, 80 to 95%, 85 to 95%, 90 to 95%, 50 to 90%, 50 to 90%, 55 to 90%, 60 to 90%, 65 to 90%, 70 to 90%, 75 to 90%, 80 to 90%, 85 to 90%, 50 to 90%, 55 to 85%, 60 to 80% or, 65 to 75% w/v or w/w of the oligomer, the remainder being comprised of pharmaceutically acceptable excipients and/or other active agents if being used.

An enteric coated tablet may also be effective in administering an alginate oligomer of the invention to the lower GI tract. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres) and/or other active agents if being used.

Enteric coated granules may also be effective in administering an alginate oligomer of the invention to the lower GI tract. Such granules may be provided in a capsule which itself may or may not be provided with an enteric coating. A representative enteric coated granule may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres) and/or other active agents if being used.

A suppository may be used to administer an alginate oligomer of the invention to the lower parts of the intestinal tract. A representative formulation may contain 1 to 25%, 1 to 20%, e.g. 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the alginate oligomer, the remainder being comprised of pharmaceutically acceptable excipients, including solid excipients (e.g. paraffin and the like), and/or other active agents if being used.

A representative aqueous solution for intravenous, intra-arterial and/or intraintestinal routes will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20%, or 15 to 25% w/v of the oligomer, the remainder being comprised of water and pharmaceutically acceptable excipients and/or other active agents if being used.

Drinking water/foodstuff containing the alginate oligomer may contain 1 to 25%, e.g. 1 to 20%, 1 to 15%, 1 to 10%, 1 to 5%, 2 to 25%, 2 to 20%, 2 to 15%, 2 to 10%, 2 to 5%, 5 to 25%, 5 to 20%, 5 to 15%, 5% to 10%, 10 to 15%, 10 to 20%, 10 to 25%, 15 to 20%, or 15 to 25% w/v of the oligomer, the remainder being comprised of water/foodstuff.

In still further embodiments of the invention the alginate oligomers may be used in the methods or uses of the invention in conjunction or combination with a further pharmaceutical (i.e. a further, or second, therapeutically active agent) for the treatment of intestinal microbial overgrowth (hereinafter "further IMO pharmaceutical").

The further IMO pharmaceutical (i.e. further therapeutically active agent active against IMO) may be an antibiotic, an antifungal, an immunostimulatory agent, a digestive enzyme supplement, a laxative agent or a mucus viscosity-reducing agent (i.e. an agent which reduces the viscosity of mucus and which terms are used interchangeably with the term "mucolytic agent").

The antibiotic may be selected from the aminoglycosides (e.g. amikacin, gentamicin, kanamycin, neomycin, netilmicin, streptomycin, tobramycin); the β-lactams (e.g. the carbecephems (e.g. loracarbef); the 1st generation cephalosporins (e.g. cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the monobactams (e.g. aztreonam); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the glycylcyclines (e.g. tigecycline); the carbapenems (e.g. imipenem, meropenem, ertapenem, doripenem, panipenem/betamipron, biapenem, PZ-601); other antibiotics include chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative immunostimulatory agents include, but are not limited to cytokines e.g. TNF, IL-1, IL-6, IL-8 and immunostimulatory alginates, such as high M-content alginates as described for example in U.S. Pat. No. 5,169,840, WO91/11205 and WO03/045402 which are explicitly incorporated by reference herein in their entirety, but including any alginate with immunostimulatory properties.

As used herein, the terms "mucolytic agent" and "mucus viscosity reducing agent" are intended to encompass agents which reduce the intrinsic viscosity of mucus and agents which reduce the attachment of mucus to underlying epithelium, in particular agents which directly or indirectly disrupt the molecular interactions within or between the components of mucus, agents which affect the hydration of mucus and agents which modulate the ionic microenvironment of the mucosal epithelium (particularly the levels of divalent cations, e.g. calcium). Representative examples of suitable mucus viscosity reducing agents include but are not limited to a nucleic acid cleaving enzyme (e.g. a DNase such as DNase I or dornase alfa), hypertonic saline, gelsolin, a thiol reducing agent, an acetylcysteine, an uncharged low molecular weight polysaccharide (e.g. dextran, mannitol), arginine (or other nitric oxide precursors or synthesis stimulators), an agonist of the P2Y2 subtype of purinergic receptors (e.g. denufosol) or an anionic polyamino acid (e.g. poly ASP or poly GLU). Ambroxol, bromhexine, carbocisteine, domiodol, eprazinone, erdosteine, letosteine, mesna, neltenexine, sobrerol, stepronin, tiopronin are specific mucolytics of note. DNase I and hypertonic saline are preferred.

Representative examples of suitable digestive enzyme supplements include but are not limited to pancrelipase (a mixture of pancreatic lipases, amylases, and chymotrypsin), pancreatin (a mixture of pancreatic lipases, amylases, and trypsin) or one or more lipases (e.g. bile salt dependent lipase, pancreatic lipase, gastric lipase, pancreatic lipase related protein 1, pancreatic lipase related protein 2, lingual lipase), proteases (e.g. pepsin, trypsin and chymotrypsin) and amylases (e.g. α-amylase, β-amylase, γ-amylase). These enzymes may be plant enzymes or animal enzymes, including human. These enzymes may be obtained from natural sources or prepared by molecular biology techniques.

Representative examples of suitable laxative agents include but are not limited to the bulk-forming laxatives (e.g. ispaghula husk, methylcellulose, ethylhydroxyethylcellulose, gum karaya, linseed fibre, wheat fibre, polycarbophil calcium); osmotic laxatives (e.g. glycerin suppositories, sorbitol, lactitol, mannitol, laminarid, lactulose, polyethylene glycol, macrogol, pentaerythritol); stimulant laxatives (e.g. bisacodyl, senna (also referred to as senna glycosides or sennosides), hydroxyanthracene glycosides, phenolphthalein, oxyphenisatine, dantron, bisoxatin, sodium picosulfate); stool softener laxatives (also referred to as emollient agents; e.g. *arachis* oil, liquid paraffin, docusate sodium (dioctyl sodium sulfosuccinate)); saline laxative agents (e.g. sodium phosphate, sodium citrate, sodium tartrate; sodium sulphate, magnesium citrate, magnesium hydroxide, magnesium sulphate, magnesium carbonate, magnesium hydroxide, magnesium oxide, magnesium peroxide); lubricant laxatives (e.g. mineral oil, glycerol); serotonin agonist laxatives (e.g. cisapride, tegaserod, prucalopride); peripheral opioid antagonist laxatives alvimopan, methylnaltrexone, naloxegol; chloride channel activator laxatives (e.g. lubiprostone); castor oil; and linaclotide.

In embodiments in which the subject has a condition arising from or associated with CFTR dysfunction in the intestinal tract, liver and/or pancreas, e.g. cystic fibrosis, the alginate oligomers may be used in the methods or uses of the invention in conjunction or combination with a CFTR modulator (also known as a "CFTR modifier").

CFTR modulators are small molecules which can redress, at least partially, a CFTR dysfunction. Present CFTR modulators fall into three main groups: CFTR potentiators, CFTR correctors and read-through agents (Derichs, N., Eur. Respir. Rev., 2013, 22(127), 58-65; Petit, R. S. and Fellner, C., Pharmacy and Therapeutics, 2014, 39(7), 500-511; the contents of which are incorporated herein by reference).

CFTR potentiators are CFTR modulators which increase the activity of the CFTR ion channel present on the epithelial cell surface. Prototypical examples of CFTR potentiators are ivacaftor (VX-770; N-(2,4-di-tert-butyl-5-hydroxyphenyl)-1,4-dihydro-4-oxoquinoline-3-carboxamide) and VRT-532 (4-methyl-2-(5-phenyl-1H-pyrazol-3-yl)-phenol) of Vertex Pharmaceuticals™)

CFTR correctors are CFTR modulators which increase the amount of CFTR protein delivered or retained at the epithelial cell surface. Prototypical examples of CFTR correctors include lumacaftor (VX-809) and VX-661 of Vertex Pharmaceuticals™ and N6022 (3-[1-(4-carbamoyl-2-methylphenyl)-5-(4-imidazol-1-ylphenyl)pyrrol-2-yl]propanoic acid).

Read-through agents (also known as "premature stop codon suppressors" (PSC suppressors) or "premature termination codon suppressors" (PTC suppressors, which terms are used interchangeably herein) are CFTR modulators which cause the translation machinery of the cell to pass over any premature termination codon in the CFTR mRNA thereby increasing the amount of substantially full length and functional CFTR produced. Prototypical examples of read-through agents include ataluren (PTC124) of PTC Therapeutics and gentamicin.

Further CFTR modulators are disclosed in WO2006002421, WO2007056341, WO2007134279, WO2009038683, WO2009064959, WO2009073757, WO2009076141, WO2009076142, WO2010019239, WO2010037066, WO2010048526, WO2010053471, WO2010054138, WO2010138484, WO2011019413, WO2011050325, WO2011072241, WO2011127241, WO2011127290, WO2011133751, WO2011133951, WO2011133953, WO2011133956, WO2011146901, Pedemonte, N., et al., J Clin Invest. 2005; 115(9):2564-2571, Van Goor, F. et al., Am J Physiol Lung Cell Mol Physiol 2006, 290: L1117-L1130, and Pedemonte, N., et al., Molecular Pharmacology, 2005 vol. 67 no. 5 1797-1807 the content of which is incorporated herein by reference.

The further IMO pharmaceutical and/or CFTR modulator may conveniently be applied in effective amounts before, simultaneously with or following the alginate oligomer. Conveniently the further IMO pharmaceutical and/or CFTR modulator is applied at substantially the same time as the alginate oligomer or afterwards. In other embodiments the further IMO pharmaceutical and/or CFTR modulator may conveniently be applied or administered before the alginate. The further IMO pharmaceutical and/or CFTR modulator can also be given (e.g. administered, applied, or delivered) repeatedly at time points appropriate for the agent used. The skilled person is able to devise a suitable dosage regimen. In long term treatments the alginate oligomer can also be used repeatedly. The alginate can be applied as frequently as the further IMO pharmaceutical and/or CFTR modulator, or more or less frequently. The frequency required may depend on the location of the microbial overgrowth being treated and also the overall nature of the clinical condition, (e.g. CF) displayed by the particular subject undergoing treatment.

The alginate oligomers proposed for use according to the invention and the further IMO pharmaceutical and/or CFTR modulator (or further therapeutically active agent), may for example be administered together, in a single pharmaceutical formulation or composition or separately (i.e. separate, sequential or simultaneous administration). Thus, effective amounts of the alginate oligomers and further IMO pharmaceutical and/or CFTR modulator may be combined, e.g. in a pharmaceutical kit or as a combined ("combination") product.

The invention therefore also provides products (e.g. a pharmaceutical kit or a combined ("combination") product) or compositions (e.g. a pharmaceutical composition) wherein the product or composition comprises an alginate oligomer and further IMO pharmaceutical and/or CFTR modulator (or further therapeutically active agent), e.g. those described above. Combinations comprising an alginate oligomer and an antibiotic, an antifungal, a laxative, a mucus viscosity reducing agent and/or CFTR modulator as herein defined or are preferred. Combinations comprising an alginate oligomer and an antibiotic, a mucus viscosity reducing agent and/or CFTR modulator as herein defined or are especially preferred. Such pharmaceutical products and pharmaceutical compositions are preferably adapted for use in the methods of the invention.

The use of alginate oligomers as herein defined to manufacture such pharmaceutical products and pharmaceutical compositions for use in the medical methods of the invention is also contemplated.

The invention will be further described with reference to the following non-limiting Examples.

EXAMPLES

Example 1—Alginate Oligomer Improves Intestinal Transit Time in CF Mice

Introduction

Decreased intestinal motility, increased intestinal transit time and intestinal obstruction are commonly seen complications of cystic fibrosis (CF). These complications lead to intestinal microbial overgrowth, e.g. Small Intestinal Bacterial Overgrowth (SIBO), Meconium Ileus (MI) and Distal Intestinal Obstruction Syndrome (DIOS).

The Cftr$^{tm1kth}$ CF mouse model (mice with the F508del mutation) displays many of the same intestinal symptoms observed in CF patients. Intestinal obstruction, which mimics MI and DIOS observed in CF patients, is the most prominent symptom displayed in CF mice making it an excellent in vivo model for testing drugs that may prevent intestinal obstruction, increase intestinal motility and decrease intestinal transit time and thereby represent a treatment for SIBO, MI or DIOS.

Methods

Wildtype (Control) and CF mice with the F508del mutation (Cftr$^{tm1kth}$) were used in the intestinal transit and survival studies. Both groups of mice were either given untreated drinking water or 2% OligoG in their drinking water for 7 days and fasted the night before intestinal motility was assessed. Data from CF mice on colyte was obtained as a reference since it is commonly used to avoid intestinal obstruction in mice.

OligoG is a 5-20mer alginate oligomer with at least 85% G residues.

Figure 1:
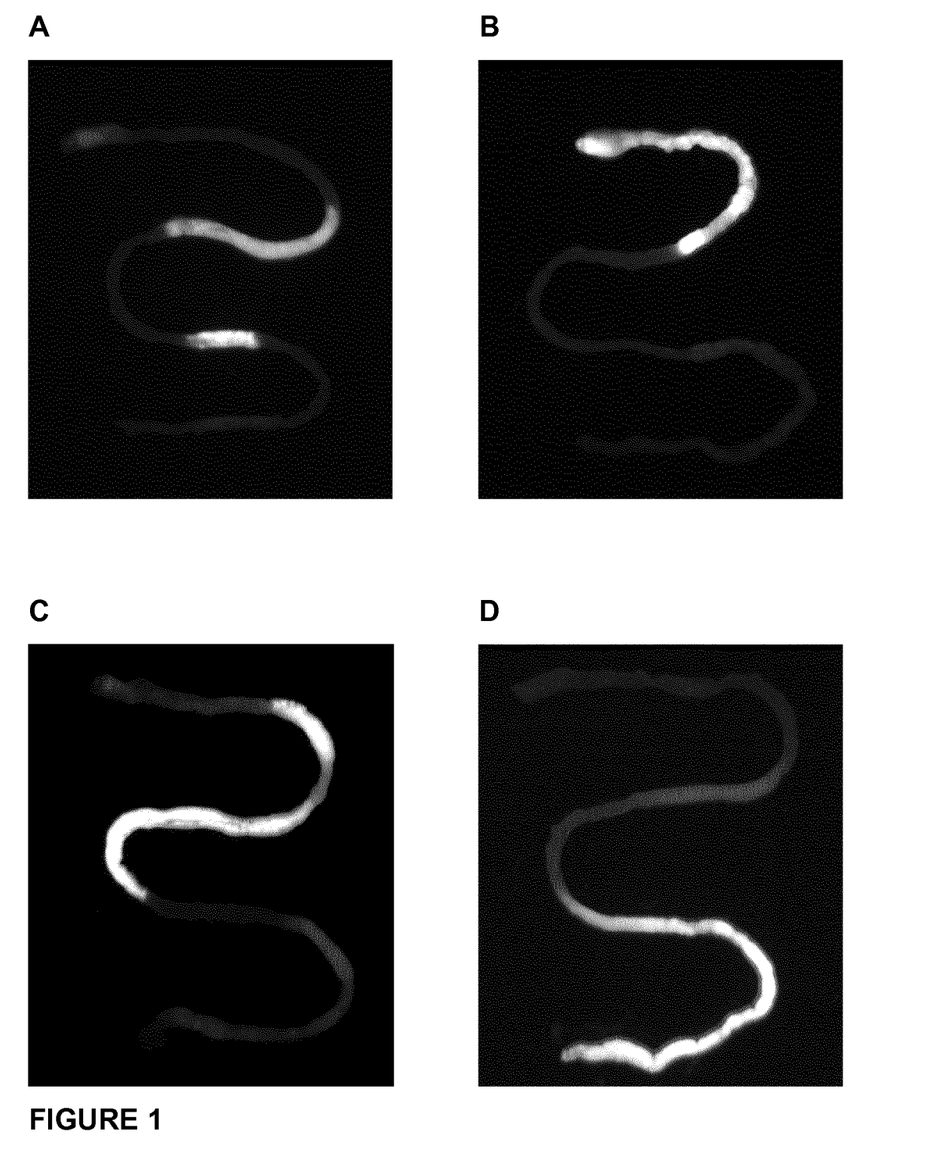
FIG. 1 shows photographs of rhodamine dextran labelled (bright white areas) small intestines of wild-type mice (A), CF mice (B) and CF mice treated with OligoG (C and D). The duodenum is at the top of each image and the ileum is at the foot of each image. Geometric centre of fluorescence (GCF) was calculated for each small intestine as 5.3, 2.9, 4.7 and 8.5, respectively.
Figure 2:
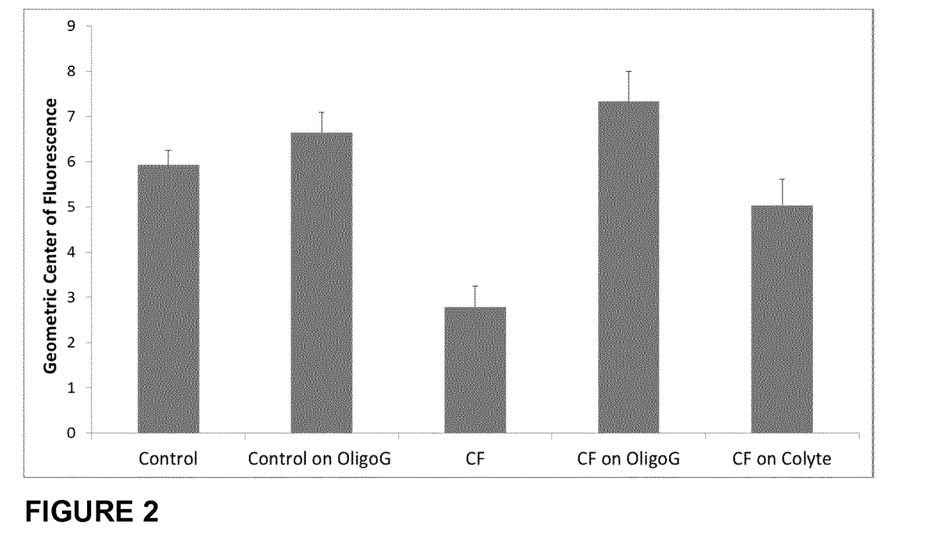
FIG. 2 shows a graphical representation of average GCF values for each group of mice on untreated water, OligoG or colyte, as described in Example 1. Control=wild-type mice; CF=CF mice. n≥5 *p<0.01 compared to Control.
Figure 3:
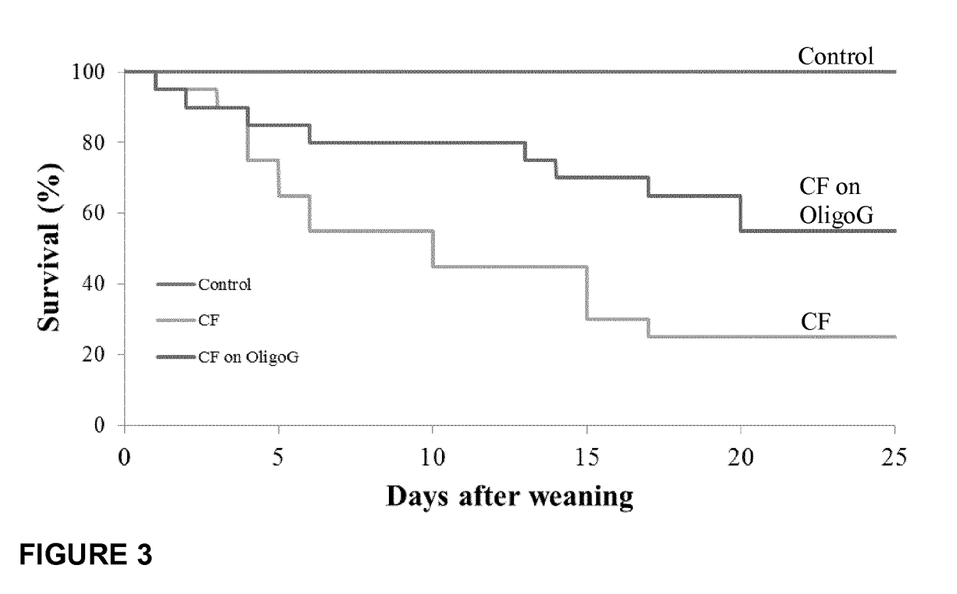
FIG. 3 shows a graphical representation of the survival of wild-type mice (Control; top trace), CF mice on untreated water (CF; bottom trace) and CF mice treated with OligoG (CF on OligoG; middle trace) in the days following weaning. n=20 *p<0.05 compared to CF.

Intestinal transit was assessed by gavaging the mice with a rhodamine dextran solution and allowing 40 minutes for the solution to travel the small intestine before sacrificing the animals. After sacrifice, the small intestines were removed, imaged (FIG. 1), and divided into 10 equal sections. Each section was flushed, contents were centrifuged and the supernatant was assessed for the amount of fluorescence per section using a fluorescence plate reader. The geometric centre of fluorescence (GCF) was calculated to provide a measure of intestinal transit in each mouse. GCF is calculated by multiplying the fluorescence per segment by the segment number (FIGS. 1 and 2).

The Ileum of Control, CF and CF mice on OligoG were analysed histologically. Sections were stained with nuclear fast red and alcian blue for mucus staining.

Survival of Control and CF mice on untreated water and CF mice treated with OligoG was assessed in the days weaning when the majority of intestinal obstruction is observed.

Results and Conclusions

OligoG improves intestinal transit time in CF mice (FIGS. 1 and 2): OligoG outperforms colyte and in some cases normalises intestinal transit time in CF mice.

OligoG decreases intestinal mucus build up in CF mice (data not shown): Alcian blue was observed between villi in ileum sections. There was noticeably more mucus staining in the CF section compared with the Control. OligoG treated CF mice appeared to show much less mucus staining than untreated CF mice.

OligoG decreases intestinal obstruction in CF mice: CF mice treated with OligoG have an improved survival and were less likely to obstruct compared to CF mice on regular water.

OligoG and other alginate oligomers may be useful for the prevention and/or treatment of intestinal obstruction, decreased intestinal motility and increased intestinal transit time in CF patients and thereby represent a treatment for SIBO, MI or DIOS in CF patients.

Example 2—Alginate Oligomers Reduce Microbial Overgrowth in CF Mice

Introduction

Decreased intestinal motility (increased intestinal transit time) is associated with intestinal microbial overgrowth in CF patients. This Example shows that alginate oligomers can not only improve intestinal transit times, but also have a positive effect in reducing microbial overgrowth.

Methods

CF mice with the F508del mutation (Cftr$^{tm1kth}$) as described in Example 1 were used in this study. Two groups of mice were each given drinking water containing either (i) 2% OligoG and 4% sucrose (test group F508del (OligoG)), or (ii) 4% sucrose (control group F508del (sucrose)), for 3 weeks. Sucrose was added to make the water more palatable to the mice.

OligoG is a 5-20mer alginate oligomer with at least 85% G residues.

Microbial load was assessed following the procedure describe in De Lisle, Am J Physio Gastroinest Liver Physiol 293: G104-G111, 2007. Briefly, the animals were sacrificed and the small intestines were removed and flushed with phosphate-buffered saline containing 10 mM dithiothreitol. The flushed material was centrifuged at 20,000 g for 30 min to pellet bacteria. The pellet was processed to extract microbial genomic DNA and microbial load was measured by quantitative PCR (qPCR) using universal bacterial 16S rRNA-specific primers as described in Nadkarni et al., Microbiology 148:257-266, 2002.

Results and Conclusions

Figure 4:
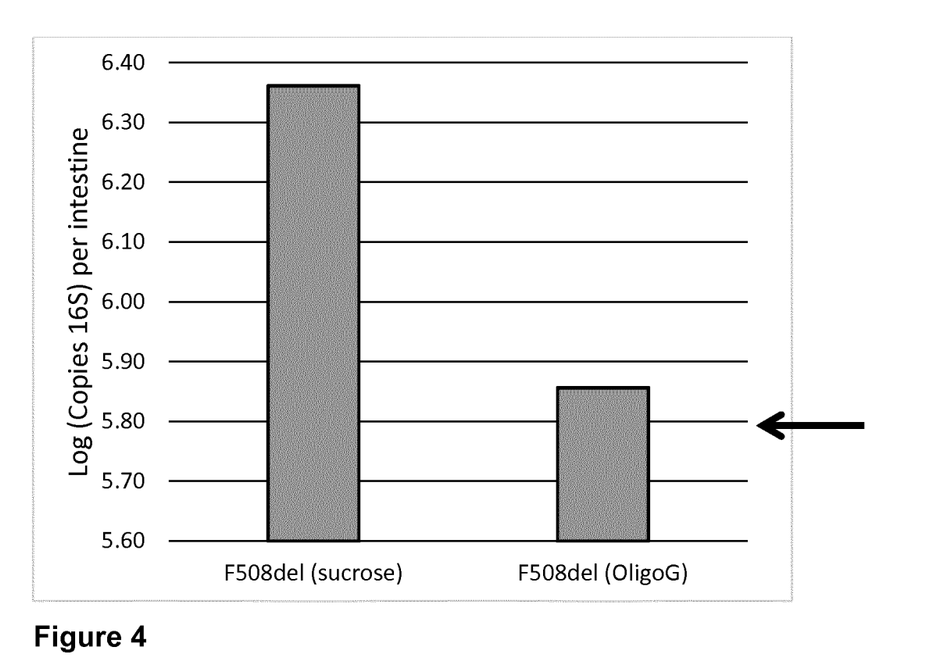
FIG. 4 shows a graphical representation of microbial growth (as measured by the number of copies of 16S rRNA present) in the intestines of mice with CF (F508del mice). Microbial growth is compared between CF mice treated with alginate oligomers and 4% sucrose (labelled "OligoG") and CF mice treated with just 4% sucrose (control group, labelled "sucrose"). Scale is $\log_{10}$. The arrow on the right indicates the baseline level for average microbial load in the murine intestine.

The results are shown in FIG. 4 which appears to indicate that OligoG may reduce microbial overgrowth in CF mice (log (copies16S) per intestine 6.36 for F508del (sucrose) control and 5.86 for F508del (OligoG)). The data are also shown in tabulated form below (Table 1).

It can be seen that F508Del mice treated with OligoG appear to show a mean decrease in 16S DNA, indicating a decrease in total microbial load. Although numbers of mice in the test and control groups were low and a high degree of variance was observed, such variance is in keeping with observations in the art regarding the presence of microbial overgrowth in CF (the presence of microbial overgrowth in CF in general is variable, so it is not surprising to see this variation in CF mice). More particularly, whilst microbial overgrowth is fairly common in CF, it does not affect all subjects, so not all of the CF mice in the study may have had microbial overgrowth. This appears to be supported by the data with both the sucrose and OligoG-treated mice in Table 1 below. The baseline level for murine microbial load in wild-type mice (according to De Lisle, Am J Physio Gastrointest Liver Physiol 293: G104-G111, 2007) is expected to be around $10^{5.8}$ (equivalent to approx. 600 000), though due to the inevitable differences between individual mice, significant variability from the average in the baseline microbial load for each individual mouse is both expected and apparent from the data below. It thus seems reasonable to assume that not all of the mice in the study were exhibiting microbial overgrowth. Thus the observed variability in the dataset supports the evidence in the literature that around 30% of CF subjects exhibit small intestinal bacterial overgrowth; only two mice, control mouse 4 and test mouse 3, in this small cohort (25%), appear to be exhibiting clear signs of overgrowth. This data also aligns with previous data in the literature (see e.g. FIG. 1 of Norkina et al., Infection and Immunity, 72(10), 6040-6049, 2004).

TABLE 1

| | F508del (sucrose) | | F508del (OligoG) |
|---|---|---|---|
| mouse 1 | 162,572 | mouse 1 | 476,083 |
| mouse 2 | 241,929 | mouse 2 | 234,584 |
| mouse 3 | 228,785 | mouse 3 | 1,444,906 |
| mouse 4 | 10,525,738 | | |
| mouse 5 | 317,612 | | |
| average | 2,295,327 | | 718,524 |
| Log 10 | 6.36 | | 5.86 |

The invention claimed is:

1. A method for the treatment of small intestinal bacterial overgrowth in a subject with small intestinal bacterial overgrowth, said treatment comprising normalizing of the time luminal contents of the small intestine take to transit the length of the small intestine of the subject, said method comprising administering to the subject an amount of alginate oligomers effective to reduce the time luminal contents of the small intestine take to transit the length of the small intestine of the subject, thereby reducing bacterial overgrowth in the small intestine of the subject,
wherein the aliginate oligomers have a number average of 2-40 monomer residues and at least 85% G residues, and
wherein the alginate oligomers are administered to the subject orally, rectally, intravenously, intra-arterially or intra-intestinally.

2. The method of claim 1, wherein said subject is a subject suffering from a condition arising from or associated with CFTR dysfunction in the intestinal tract, liver and/or pancreas, scleroderma, celiac disease, inflammatory bowel disease (IBD) and its subtypes Crohn's disease and ulcerative colitis, and diabetes mellitus type 1 and type 2.

3. The method of claim 2, wherein said condition arising from or associated with CFTR dysfunction in the intestinal tract, liver and/or pancreas is cystic fibrosis.

4. The method of claim 1, wherein the alginate oligomers have a degree of polymerization (DP), or a number average degree of polymerization (DPn) of 4 to 35.

5. The method of claim 1, wherein the alginate oligomers have at least 90% G residues.

6. The method of claim 1, wherein at least 80% of the G residues of the alginate oligomers are arranged in G-blocks.

7. The method of claim 1, wherein the alginate oligomers have a number average degree of polymerization in the range 5 to 20, a guluronate fraction ($F_G$) of at least 0.85 and a mannuronate fraction ($F_M$) of no more than 0.15.

8. The method of claim 1 wherein said alginate oligomers have saturated terminal uronic acid residues.

9. The method of claim 1 wherein said alginate oligomers are prepared by acid hydrolysis of an alginate polysaccharide.

10. The method of claim 1 wherein said alginate alginate oligomers are administered enterally, parenterally, or by inhalation.

11. The method of claim 10, wherein said enteral administration is oral administration.

12. The method according to claim 1, wherein the alginate oligomers have an average molecular weight of 2600 Da and at least 85% G residues.

* * * * *